(12) United States Patent
Angermeier et al.

(10) Patent No.: US 10,470,844 B2
(45) Date of Patent: Nov. 12, 2019

(54) DENTAL OR DENTAL SURGICAL ULTRASONIC TOOL

(71) Applicant: W&H Dentalwerk Bürmoos GmbH, Bürmoos (AT)

(72) Inventors: Bernd Angermeier, Lamprechtshausen (AT); Wilhelm Brugger, Wals-Siezenheim (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 0 days.

(21) Appl. No.: 15/889,030

(22) Filed: Feb. 5, 2018

(65) Prior Publication Data

US 2018/0153642 A1  Jun. 7, 2018

Related U.S. Application Data

(63) Continuation of application No. PCT/EP2016/069191, filed on Aug. 12, 2016.

(30) Foreign Application Priority Data

Aug. 12, 2015  (EP) .................................. 15180669

(51) Int. Cl.
*A61C 3/03*  (2006.01)
*A61C 1/00*  (2006.01)
(Continued)

(52) U.S. Cl.
CPC .............. *A61C 3/03* (2013.01); *A61C 1/0069* (2013.01); *A61C 1/148* (2013.01); *A61C 17/20* (2013.01); *A61C 1/055* (2013.01); *A61C 8/0092* (2013.01)

(58) Field of Classification Search
CPC .............. A61C 3/03; A61C 1/07; A61C 1/055
See application file for complete search history.

(56) References Cited

U.S. PATENT DOCUMENTS

| 4,021,920 | A |   | 5/1977 | Kirschner et al. |
| 4,911,639 | A | * | 3/1990 | Jacklich ................... A61C 1/07 433/102 |

(Continued)

FOREIGN PATENT DOCUMENTS

| EP | 1974680 | 10/2008 |
| KR | 10-2013-0094985 | 8/2013 |

(Continued)

OTHER PUBLICATIONS

International Search Report for PCT/EP2016/069191, dated Nov. 15, 2016.

*Primary Examiner* — Ralph A Lewis
(74) *Attorney, Agent, or Firm* — Klarquist Sparkman, LLP

(57) ABSTRACT

A dental or dental surgical ultrasonic tool, comprising: a tool body, a connecting device for connection to an ultrasonic source, a working section extending along a longitudinal axis and designed to penetrate into bone to be treated, and a liquid line extending through the tool body in the direction of the working section and ending in at least one opening for the discharge of a liquid, wherein the working section has a distal end face with multiple cutting edges and a lateral surface connected thereto, wherein at least one channel for conveying a liquid is provided in the lateral surface, and wherein the at least one opening of the liquid line is disposed on the lateral surface in the at least one channel or directly adjacent to the at least one channel. Additionally or alternatively, the at least one channel extends helically around the longitudinal axis of the working section.

20 Claims, 1 Drawing Sheet

(51) Int. Cl.
  *A61C 1/14*  (2006.01)
  *A61C 17/20* (2006.01)
  *A61C 1/05*    (2006.01)
  *A61C 8/00*    (2006.01)

(56) References Cited

U.S. PATENT DOCUMENTS

| | | |
|---|---|---|
| 5,022,857 A | 6/1991 | Matsutani et al. |
| 5,575,650 A | 11/1996 | Niznick et al. |
| 8,109,931 B2 | 2/2012 | Vercellotti et al. |
| 2010/0178631 A1 | 7/2010 | Gordils Wallis et al. |
| 2011/0143308 A1* | 6/2011 | Lee .................. A61B 17/1644 |
| | | 433/80 |
| 2011/0229845 A1 | 9/2011 | Chen |

FOREIGN PATENT DOCUMENTS

| | | |
|---|---|---|
| KR | 10-2014-0105744 | 9/2014 |
| WO | WO2008/038307 | 4/2008 |

\* cited by examiner

DENTAL OR DENTAL SURGICAL ULTRASONIC TOOL

CROSS REFERENCE TO RELATED APPLICATION

This application is a U.S. bypass continuation application of International Application No. PCT/EP2016/069191, filed Aug. 12, 2016, which in turn claims priority from pending European Patent Application No. 15180669.2, filed Aug. 12, 2015, which are incorporated herein by reference.

BACKGROUND

Field

The invention relates to a dental or dental surgical ultrasonic tool, comprising an elongated tool body, a connecting device for releasable connection to an ultrasonic source, a liquid line and a working section which is designed to penetrate into a bone to be treated by ultrasonic vibrations transmitted by the ultrasonic source.

Description of Prior Art

Such a dental or dental surgical ultrasonic tool is known from U.S. Pat. No. 8,109,931 B2. To supply cooling liquid to the treatment site, an opening connected to the liquid line is provided on the distal end of the working section.

SUMMARY

It would be advantageous to create a dental or dental surgical ultrasonic tool having an improved distribution of the cooling liquid, an improved cooling effect for the entire tip and improved handling.

These and other advantages are achieved according to the present invention by a dental or dental surgical ultrasonic tool having the features described below.

According to a first embodiment, the dental or dental surgical ultrasonic tool comprises an elongated tool body, a connecting device for releasable connection of the ultrasonic tool to an ultrasonic source, wherein the connecting device is provided on a first end of the tool body, a working section provided on a second end of the tool body, extending along a longitudinal axis and designed to penetrate into a bone to be treated due to the ultrasonic vibrations generated by the ultrasonic source and transmitted via the connecting device and the tool body, and a liquid line extending through the tool body in the direction of the working section and ending in at least one opening which is provided for discharge of a liquid flowing in the liquid line out of the ultrasonic tool. The working section comprises a distal end face having a plurality of cutting edges and a lateral surface extending from the distal end face in the direction of the tool body, wherein at least one channel for conveying a liquid is provided in the lateral surface, extending from the distal end face in the direction of the tool body. The at least one opening of the liquid line is disposed on the lateral surface of the working section in the at least one channel for conveying a liquid or directly adjacent to the at least one channel for conveying a liquid.

Providing the at least one opening of the liquid line, preferably multiple openings, on the lateral surface of the working section produces a better distribution of cooling liquid on the entire working section and thus a stronger cooling effect, in particular when the working section has already entered the bone, and therefore cooling is advantageous not only on the distal end face but also on the lateral surface of the working section. Due to the arrangement of the at least one opening of the liquid line, preferably multiple openings in or directly adjacent to the at least one channel for conveying a liquid, it is ensured that the liquid will reach the distal end face and thus also the treatment site, so that these two regions are also adequately supplied with liquid and cooled.

The at least one channel for conveying a liquid according to this first embodiment is either straight, i.e., essentially parallel to the longitudinal axis of the working section, or is helically formed around the longitudinal axis of the working section, as described in detail below.

According to a second embodiment, the dental or dental surgical ultrasonic tool comprises an elongated tool body, a connecting device for releasable connection of the ultrasonic tool to an ultrasonic source, wherein the connecting device is provided on a first end of the tool body, a working section, which is provided on a second end of the tool body, extends along a longitudinal axis and is designed to penetrate into a bone to be treated based on the ultrasonic vibrations generated by the ultrasonic source and transmitted via the connecting device and the tool body, and a liquid line extending through the tool body in the direction of the working section and ending in at least one opening provided for discharge of a liquid flowing in the liquid line out of the ultrasonic tool. The working section comprises a distal end face having a plurality of cutting edges and a lateral surface extending from the distal end face in the direction of the tool body, wherein at least one channel for conveying a liquid is provided in the lateral surface, extending helically around the longitudinal axis of the working section from the distal end face in the direction of the tool body.

Due to the helical design of the at least one channel for conveying a liquid, an improved shaping of the cavity in the bone and facilitated handling of the ultrasonic tool are achieved in particular: since during operation the ultrasonic tool primarily vibrates forward and backward along the longitudinal axis of the working section, a smoother or more homogeneous cut in the bone (on the side wall of the cavity) is achieved, as seen over the entire circumference of the bone, due to the provision of the at least one helical channel, in comparison with a channel running parallel to the longitudinal axis of the working section. In order to achieve a uniform shaping of the cavity formed by the ultrasonic tool in the bone, the user will rotate the ultrasonic tool about the longitudinal axis of the working section, while the ultrasonic tool is penetrating into the hone. This rotation by the user is also facilitated (it is less "jerky") because the cut in the bone is smoother or more homogeneous due to the at least one helical channel.

Each of the properties and features mentioned below refers to both of the embodiments referenced above.

The dental or dental surgical ultrasonic tool is preferably made of metal, in particular steel.

The elongated tool body is preferably designed to be cylindrical on at least one section or over its entire length. The elongated tool body preferably comprises a bend, so that the tool body has in particular two sections disposed at an angle to one another. The angle of these two sections to one another amounts to between 5° and 90°, for example, preferably between 10° and 75°.

The connecting device is designed for releasable connection of the ultrasonic tool to an ultrasonic source and in particular also for releasable connection to a liquid source. The connecting device comprises, for example, a tubular element having an inside bore and an inside thread provided on the wall of the inside bore. The connecting device and the ultrasonic tool thus can be screwed onto a threaded pin that can be accommodated in the inside bore and is connected to an ultrasonic source and in particular to a liquid source. The threaded pin is preferably part of a handpiece that can be held with a hand.

The connecting device preferably comprises a larger outside diameter than the tool body and is connected to the first end of the tool body, in particular by means of a tapering section, which preferably has at least one abutting surface for a tool for screwing the ultrasonic tool onto the threaded pin.

The working section provided on a second end of the tool body has an essentially cylindrical outside circumference. The length of the working section is preferably several times smaller than the length of the tool body. The axial extent of the working section along its longitudinal axis preferably extends from a free end of the ultrasonic tool where the distal end face is disposed in particular, up to at least the end of the at least one channel for conveying a liquid which faces the connected tool body. The outside diameter of the working section is preferably approximately the same size or larger than the outside diameter of the tool body. In the latter case a tapering transitional section to the elongated tool body is preferably provided which is optionally designed as part of the working section or connected thereto.

The working section comprises a distal end face with a plurality of cutting edges and a lateral surface extending from the distal end face in the direction of the tool body, wherein at least one channel for conveying a liquid is provided in the lateral surface, which is preferably designed to be essentially cylindrical, said channel extending from the distal end face in the direction of the tool body.

Depending on the embodiment, the at least one channel for conveying a liquid is either designed to be straight, i.e., essentially parallel to the longitudinal axis of the working section, or is designed helically around the longitudinal axis of the working section. The at least one channel preferably ends at the distal end face and/or is connected to it in such a way that liquid flowing in the channel can be transferred or further diverted to the distal end face and/or to the treatment site and/or liquid from the distal end face and/or the treatment site can enter into the at least one channel.

Adjacent to the at least one channel, in particular in the circumferential direction laterally of the channel, preferably at least one web is provided on the working section. When multiple channels are present on the working section, one web separates two channels from one another. The course of the at least one web preferably corresponds essentially to that of the at least one channel, i.e., the at least one web is either designed to be essentially parallel to the longitudinal axis of the working section or is designed helically around the longitudinal axis of the working section. Accordingly, the at least one web preferably ends at the distal end face or forms a joint edge together with the distal end face. At least one cutting edge of the distal end face is especially preferably connected to the free distal end of the at least one web. The at least one web is preferably elevated with respect to the at least one channel or the at least one channel is shaped as a recess relative to the at least one web.

The cutting edges preferably extend radially away from a midpoint of the distal end face in the direction of the periphery of the distal end face or in the direction of the lateral surface. Preferably each cutting edge forms a ridge or peak of two surfaces of the cutting edge that are inclined in the direction of the distal end face or of the tool body. Each one of these inclined surfaces preferably comes in contact with another inclined surface of the most proximate cutting edge at its lowest point, thus forming a recess or a trough between two neighboring cutting edges. This recess or trough is preferably provided for carrying liquid, as described in detail below.

The free or distal end section of the at least one web at a circumferential edge of the distal end face is preferably connected mainly to a cutting edge and its inclined surfaces. The at least one channel is preferably connected at a peripheral edge of the distal end face to the recess or the trough in such a manner that liquid can be transferred.

The liquid line extending through the tool body in the direction of the working section is preferably designed as a cylindrical bore in the tool body. The liquid line ends in at least one opening which is provided for discharge of a liquid flowing in the liquid line out of the ultrasonic tool. The liquid line is connected to the connecting device, in particular to its inside bore or is continued in the inside bore of the connecting device. If the liquid line ends in multiple openings for the discharge of a liquid, then the liquid line branches off, in particular in the area of the working section or directly adjacent to same, preferably into a plurality of line branches for supplying the plurality of openings.

The at least one opening provided for the discharge of a liquid flowing in the liquid line out of the ultrasonic tool is optionally disposed on the lateral surface of the working section or on the distal end face. The at least one opening is preferably disposed on the lateral surface in the at least one channel for conveying a liquid or directly connected to the at least one channel for conveying a liquid or at the center of the distal end face.

A plurality of openings, for example, two, three or four openings, are preferably provided for discharge of a liquid flowing in the liquid line out of the ultrasonic tool. These openings may optionally all be disposed on the lateral surface of the working section, in particular in multiple channels for conveying a liquid or directly connected to these channels. By providing multiple openings of the liquid line on the lateral surface of the working section, an improved distribution of the liquid on the lateral surface or the circumference of the ultrasonic tool is achieved in particular. Alternatively, at least one opening, preferably multiple openings, are provided on the lateral surface of the working section, in particular in one or more channels for conveying a liquid or directly connected to this channel or these channels, and at least one (additional) opening of the liquid line is provided on the distal end face. This achieves a particularly good supply of the entire working section, including the distal end face with liquid and a particularly good cooling performance.

A plurality of channels, particularly extending in a helix around the longitudinal axis of the working section and several openings of the liquid line are preferably provided, wherein only one opening is provided in or at each channel.

Preferably at least in or at one channel extending in particular in a helical form around the longitudinal axis of the working section there is not provided an opening of the liquid line. In particular the number of openings of the liquid line which are disposed in or at a channel extending in particular in a helical form around the longitudinal axis of the working section is lower than the number of (all) the channels, so that at least in and at one channel there is not provided an opening of the liquid line. This at least one channel extending in particular in a helical form around a longitudinal axis of the working section without openings of the liquid line is designed in particular to convey liquid away from the distal end face and/or the treatment site.

The at least one channel extending in particular in a helical form around the longitudinal axis of the working section has a depth that increases in the direction of the distal end face. The increase in the depth in the direction of the distal end face amounts to between 4% and 25%, preferably between 5% and 15%, for example (starting from the lowest depth). The increasing depth of the at least one channel produces a preferred flow of the liquid in the channel, in particular the liquid emerging from the openings of the liquid line and forwarded through the channel in the direction of the distal end face. Preferably at least one channel has a constant depth, in particular a channel which is designed to convey liquid away from the distal end face and/or the treatment site, for example, a channel, as identified above, without any openings of the liquid line.

The slope of the at least one channel extending in a helical form around the longitudinal axis of the working section amounts to about 5 mm-50 mm, preferably about 15 mm-25 mm. The slope defines the length of the path or the helical channel traveled through a complete revolution (by 360°) of the working section, in particular the helical channel. The conical thread rise or the taper of the helical channel in the direction of the distal end face preferably amounts to about 3%-25%, in particular about 5%-15%, preferably between 8%-9%.

The at least one helical channel preferably winds around the longitudinal axis of the working section with an angle of rotation in the range between 45° and 180°. For example, the at least one helical channel winds around the longitudinal axis of the working section with an approximate ⅛ to ¼ rotation.

The at least one opening of the liquid line is preferably provided in the half of the at least one channel which extends in particular in a helical form around the longitudinal axis of the working section which is disposed closer to the distal end face. It is thus possible to achieve an optimal supply and cooling of the lateral surface of the working section, of the bone layer adjacent thereto, the distal end face and the bone surface thereby processed.

As already described above, troughs for carrying liquid, connected to or opening into the at least one channel, extending in particular in a helical form around the longitudinal axis of the working section, are provided on the distal end face between the cutting edges. The troughs are formed in particular by surfaces arising from the cutting edges and inclined in the direction of the lateral surface of the working section or of the tool body. The troughs permit optimal conveyance of the liquid from the at least one opening of the liquid line through the at least one channel up to the distal end face and/or the treatment site and/or optimal drainage of the liquid and in particular the particles contained therein, for example, bone particles abraded from the cutting edges, away from the distal end face and/or the treatment site (in the direction of the tool body).

The troughs for carrying liquid, in particular according to the cutting edges, preferably extend radially from a midpoint of the distal end face in the direction of the periphery of the distal end face. The distal end face is thus designed in a star shape with troughs and cutting edges starting from the midpoint of the distal end face and disposed in alternation. The cutting edges and the troughs for carrying liquid are preferably inclined in the direction of a recess disposed centrally in the distal end face. An opening of the liquid line is especially preferably provided in the midpoint or recess in the distal end face.

A liquid path, comprising the following elements that were mentioned above is preferably formed on the ultrasonic tool: the liquid line, the at least one opening for discharging a liquid flowing in the liquid line out of the ultrasonic tool, the at least one channel extending in particular helically around the longitudinal axis of the working section, and the troughs for carrying liquid on the distal end face. The liquid path is designed in particular to carry a liquid through the aforementioned elements of the ultrasonic tool to the distal end face and/or a treatment site, so that excellent cooling of the entire working section and distribution of the liquid to the bone to be treated and the working section are possible.

The liquid path additionally comprises at least one channel extending in particular in a helical form around the longitudinal axis of the working section, designed to carry liquid away from the distal end face and/or the treatment site. In particular no opening for the discharge of a liquid flowing in the liquid line is provided in or at this at least one channel for carrying away the liquid. In particular material abraded by the cutting edge is also entrained by the liquid and removed from the treatment site, so that the abrasion effect of the cutting elements is improved.

A coating to prevent corrosion, for example, a titanium nitride coating, is preferably provided on at least one section of the ultrasonic tool, in particular on the working section and/or on at least a portion of the body.

A dental or dental surgical treatment device comprises an ultrasonic tool as described above and an ultrasonic source for generating ultrasonic vibrations, which can be connected to the ultrasonic tool so that the ultrasonic vibrations generated by the ultrasonic source can be transferred to the ultrasonic tool. The ultrasonic source is designed as a piezo oscillator, for example, or as a magnetostrictive oscillator. The ultrasonic source is preferably disposed in a dental or dental surgical handpiece.

The treatment device or the handpiece comprises preferably at least one additional component of the following components: a tool connecting device for releasable connection to the ultrasonic tool, comprising in particular the threaded pin described above; an electrical or electronic controller for operation of the treatment device or the handpiece, in particular the ultrasonic source; an oscillation transmitter or a sonotrode for transmitting the ultrasonic oscillations generated by the ultrasonic source to the ultrasonic tool; a lighting device preferably with LEDs, in particular with an ring-shaped light-emitting face on the end facing the treatment site during operation, wherein the ring-shaped light-emitting surface surrounds the ultrasonic tool; at least one line for transferring the liquid from a liquid source to the ultrasonic tool.

These and other embodiments will be described below with reference to the following drawings.

DETAILED DESCRIPTION

Figure 1:
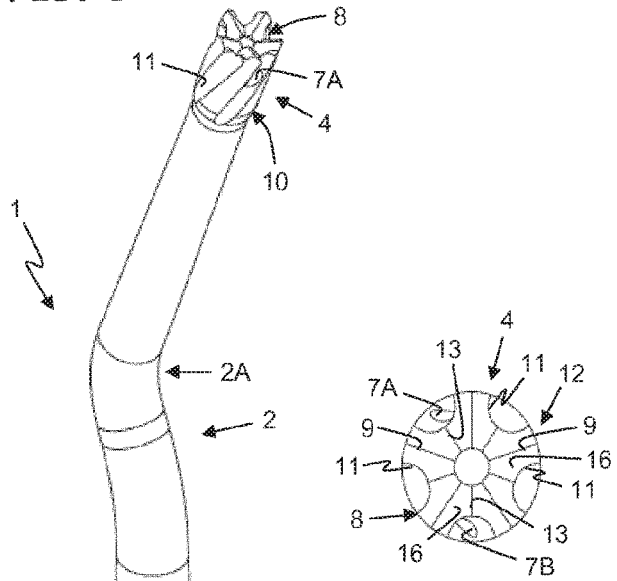
FIG. 1 shows a perspective view of a dental or dental surgical ultrasonic tool.
Figure 2:
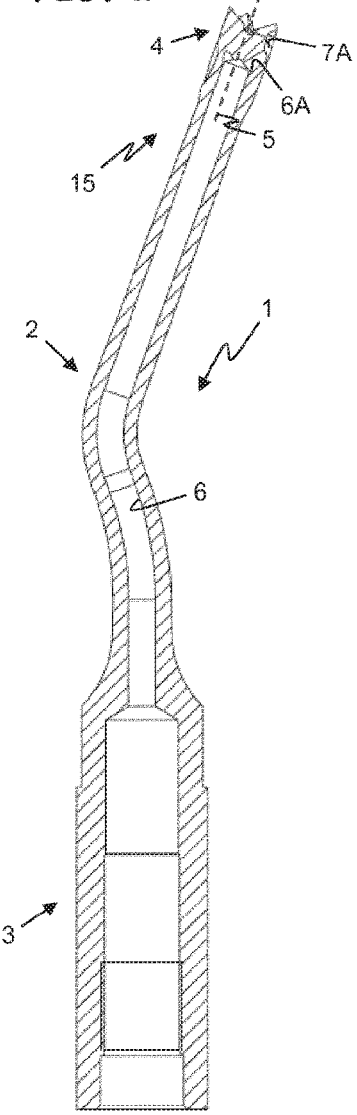
FIG. 2 shows a sectional view through the ultrasonic tool of FIG. 1.
Figure 4:
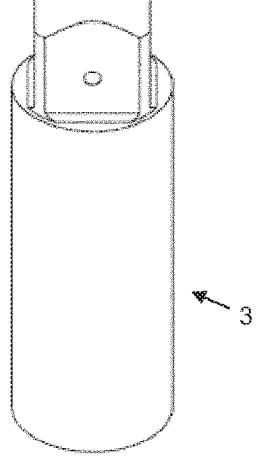
FIG. 4 shows a front view of the working section of the ultrasonic tool of FIG. 1.
Figure 3:
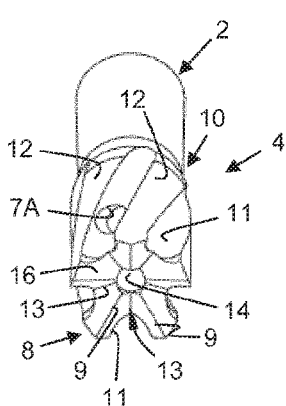
FIG. 3 shows an enlarged view of the distal end section of the ultrasonic tool of FIG. 1.

The dental or dental surgical ultrasonic tool 1 illustrated in FIGS. 1-4 comprises an elongated tool body 2, a connecting device 3 for releasable connection of the ultrasonic tool 1 to an ultrasonic source, a working section 4 extending along a longitudinal axis 5 and designed to penetrate into the bone to be treated based on the ultrasonic vibrations generated by the ultrasonic source and transmitted via the connecting device 3 and the tool body 2, and a liquid line 6 extending through the tool body 2 in the direction of the working section 4 and ending in a plurality of openings 7A, 7B, for example two openings 7A, 7B, which are provided for the discharge of a liquid flowing in the liquid line 6 out of the ultrasonic tool 1.

To facilitate the handling of the ultrasonic tool 1, the elongated tool body 2 comprises a bend 2A so that the working section 4 or its longitudinal axis 5 is disposed at an angle to the connecting device 3. The elongated tool body 2 additionally comprises a first end, on which the connecting device 3 is provided and a second end, to which the working section 4 is connected.

The working section 4 comprises a distal end face 8 having multiple cutting edges, for example, five cutting edges 9 and a lateral surface 10 extending from the distal end face 8 in the direction of the tool body 2. A plurality of channels, for example, five channels 11 for carrying liquid are provided in the lateral surface 10. The channels 11 each extend from the distal end face 8 in the direction of the tool body 2. The channels 11 are distributed on the lateral surface 10 spaced a uniform distance away from one another.

The liquid line 6 opens with its openings 7A, 7B on the lateral surface 10 of the working section 4. The openings 7A, 7B are disposed in the channels 11, wherein only one opening 7A, 7B is arranged in one respective channel 11. As can be seen in particular from FIGS. 3 and 4, an opening 7A, 7B is provided only in each of two channels 11 while the other three helical channels 11 do not have an opening 7A, 7B of the liquid line 6. The helical channels with the openings 7A, 7B are preferably separated by at least one helical channel 11 without openings 7A, 7B.

The connection between the liquid line 6 disposed substantially centrally in the tool body 2 and the openings 7A, 7B is accomplished by several line branches 6A, wherein each one of the openings 7A, 7B is connected to the liquid line 6 via a separate line branch 6A. The line branches 6A are disposed at an angle to the liquid line 6.

The channels 11 for conveying a liquid extend in a helix around the longitudinal axis 5 of the working section 4 with an angle of rotation of approx. 70°, The helical channels 11 are separated from one another by webs 12, which also have a helical form. The channels 11 are designed to be recesses in the lateral surface 10 with respect to the webs 12.

On the distal end face 8 between the cutting edges 9 a plurality of troughs, for example, five troughs 13 are provided for carrying liquid. The troughs 13 are formed by surfaces 16 that arise from the cutting edges 9 and are inclined in the direction of the lateral surface 10 of the working section 4 or of the tool body 2. Each trough 13 is connected to one respective channel 11 extending in the form of a helix around the longitudinal axis 5 of the working section 4. The cutting edges 9 and the troughs 13 for carrying liquid extend radially from a midpoint on the distal end face 8. The cutting edges 9 and the troughs 13 are additionally inclined in the direction of a recess 14 disposed centrally around the midpoint of the distal end face 8. The liquid line 6, the two openings 7A, 7B for the discharge of a liquid flowing in the liquid line 6, the channels 11 extending in a helical form around the longitudinal axis 5 of the working section 4, in particular the channels 11 in or at which the openings 7A, 7B are disposed, and the troughs 13 on the distal end face 8 together form a liquid path 15 for carrying a liquid from the liquid line 6 to the distal end face 8 and/or to a treatment site and cooling the working section 4 and the treatment site. In particular the helical channels 11, which do not have any openings 7A and 7B and are part of the liquid path 15, are provided for carrying the liquid away from the distal end face 8 and/or the treatment site in the direction of the tool body 2.

The invention is not limited to the embodiments described here, but instead includes all embodiments that apply or include the basic analogous function principle of the invention according to the claims. In addition, each feature that is described or illustrated can be combined with any other feature described or illustrated.

What is claimed is:

1. A dental or dental surgical ultrasonic tool, comprising:
   an elongated tool body,
   a connecting device for releasable connection of the ultrasonic tool to an ultrasonic source, wherein the connecting device is provided on a first end of the tool body,
   a working section which extends along a longitudinal axis and is provided on a second end of the tool body and is designed to penetrate into bone to be treated based on ultrasonic vibrations generated by the ultrasonic source and transmitted via the connecting device and the tool body, and
   a liquid line extending through the tool body in the direction of the working section and ending in at least one opening, which is provided for the discharge of a liquid flowing in the liquid line out of the ultrasonic tool, wherein
   the working section comprises a distal end face with a plurality of cutting edges and a cylindrical lateral surface extending from the distal end face in the direction of the tool body and having a substantially constant outer diameter relative to the longitudinal axis of the working section, wherein
   at least one channel for conveying a liquid is provided in the cylindrical lateral surface, extending from the distal end face in the direction of the tool body, wherein
   the at least one opening of the liquid line is disposed on the cylindrical lateral surface of the working section in or directly adjacent to the at least one channel for conveying a liquid, and wherein
   the at least one channel for conveying a liquid extends in a helical form around the longitudinal axis of the working section.

2. The dental or dental surgical ultrasonic tool according claim 1, wherein the at least one channel for conveying a liquid is one of a plurality of channels for conveying a liquid which are separated from one another by webs.

3. The dental or dental surgical ultrasonic tool according to claim 1, wherein the at least one channel for conveying a liquid is one of a plurality of channels for conveying a liquid and the at least one opening provided for the discharge of a liquid flowing in the liquid line is one of a plurality of openings of the liquid line, wherein only one opening is arranged in or directly adjacent to one respective channel.

4. The dental or dental surgical ultrasonic tool according to claim 1, wherein the at least one channel for conveying a liquid is one of a plurality of channels for conveying a liquid and wherein at least one channel of the plurality of channels does not have an opening of the liquid line which is in or directly adjacent to said at least one channel.

5. The dental or dental surgical ultrasonic tool according to claim 1, wherein the at least one opening of the liquid line is provided in a half of the at least one channel which is disposed closer to the distal end face.

6. The dental or dental surgical ultrasonic tool according to claim 1, wherein at least one trough for carrying liquid is provided on the distal end face between the cutting edges and connects to or opens into the at least one channel.

7. The dental or dental surgical ultrasonic tool according to claim 6, comprising
  a liquid path formed on the ultrasonic tool, comprising
    the liquid line,
    the at least one opening for the discharge of a liquid flowing in the liquid line out of the ultrasonic tool,
    the at least one channel, and
    the at least one trough for carrying liquid on the distal end face, wherein
    the liquid path is configured to carry a liquid through the liquid line, the at least one opening, the at least one channel, and the at least one trough to convey liquid to the distal end face and/or a treatment site.

8. The dental or dental surgical ultrasonic tool according to claim 7, wherein the liquid path further comprises an additional channel on the cylindrical lateral surface of the working section configured to carry liquid away from the distal end face and/or the treatment site, wherein the additional channel does not have an opening of the liquid line which is in or directly adjacent to said at least one channel.

9. A dental or dental surgical ultrasonic tool, comprising:
  an elongated tool body,
  a connecting device for releasable connection of the ultrasonic tool to an ultrasonic source, wherein the connecting device is provided on a first end of the tool body,
  a working section which extends along a longitudinal axis and is provided on a second end of the tool body and is designed to penetrate into bone to be treated on the basis of ultrasonic vibrations generated by the ultrasonic source and transmitted via the connecting device and the tool body, and
  a liquid line which extends through the tool body in the direction of the working section and ends in at least one opening provided for the discharge of a liquid flowing in the liquid line out of the ultrasonic tool, wherein
  the working section comprises a distal end face with multiple cutting edges and a lateral surface extending from the distal end face in the direction of the tool body, wherein
  at least one channel for conveying a liquid is provided in the lateral surface, extending from the distal end face in the direction of the tool body, wherein
  the at least one channel for conveying a liquid extends in a helical form around the longitudinal axis of the working section.

10. The dental or dental surgical ultrasonic tool according claim 9, wherein the at least one channel for conveying a liquid is one of a plurality of channels for conveying a liquid extending in a helical form around the longitudinal axis of the working section and which are separated from one another by webs having a helical form.

11. The dental or dental surgical ultrasonic tool according to claim 9, wherein the at least one channel for conveying a liquid is one of a plurality of channels for conveying a liquid which extend in a helical form around the longitudinal axis of the working section and wherein the at least one opening provided for the discharge of a liquid is arranged in or directly adjacent to one channel of the plurality of channels.

12. The dental or dental surgical ultrasonic tool according to claim 11, wherein the at least one opening of the liquid line is provided in a half of the at least one channel which is disposed closer to the distal end face.

13. The dental or dental surgical ultrasonic tool according to claim 9, wherein the channel extending in a helical form around the longitudinal axis of the working section has a depth that increases in the direction of the distal end face.

14. The dental or dental surgical ultrasonic tool according to claim 9, wherein a slope of the at least one channel extending in a helical form around the longitudinal axis of the working section amounts to approx. 5 mm-50 mm.

15. The dental or dental surgical ultrasonic tool according to claim 9, wherein the at least one channel extending in a helical form around the longitudinal axis of the working section winds at a rotational angle in the range between 45° and 180° around the longitudinal axis.

16. The dental or dental surgical ultrasonic tool according to claim 9, wherein at least one trough for carrying liquid is provided on the distal end face between the cutting edges and connects to or opens into the at least one channel.

17. The dental or dental surgical ultrasonic tool according to claim 16, wherein the cutting edges and the at least one trough for carrying liquid extend radially out from a midpoint on the distal end face.

18. The dental or dental surgical ultrasonic tool according to claim 16, wherein the cutting edges and the at least one trough for carrying liquid are inclined in the direction of a recess disposed centrally in the distal end face.

19. A dental or dental surgical treatment device, comprising an ultrasonic tool according to claim 9 and an ultrasonic source for generating ultrasonic vibrations which can be connected to the ultrasonic tool so that the ultrasonic vibrations generated by the ultrasonic source can be transmitted to the ultrasonic tool.

20. A dental or dental surgical ultrasonic tool, comprising:
  an elongated tool body,
  a connecting device for releasable connection of the ultrasonic tool to an ultrasonic source, wherein the connecting device is provided on a first end of the tool body,
  a working section which extends along a longitudinal axis and is provided on a second end of the tool body and is designed to penetrate into bone to be treated based on ultrasonic vibrations generated by the ultrasonic source and transmitted via the connecting device and the tool body, and
  a liquid line extending through the tool body in the direction of the working section and ending in at least one opening, which is provided for the discharge of a liquid flowing in the liquid line out of the ultrasonic tool, wherein
  the working section comprises a distal end face with a plurality of cutting edges and a cylindrical lateral surface extending from the distal end face in the direction of the tool body and having a substantially constant outer diameter relative to the longitudinal axis of the working section, wherein
  at least one channel for conveying a liquid is provided in the cylindrical lateral surface, extending from the distal end the in the direction of the tool body, wherein
  the at least one opening of the liquid line is disposed on the cylindrical lateral surface of the working section in or directly adjacent to the at least one channel for conveying a liquid, wherein
  the at least one channel for conveying a liquid extends in a helical form around the longitudinal axis of the working section, wherein the at least one channel for conveying a liquid is one of a plurality of channels for conveying a liquid Which are separated from one another by webs, and wherein the at least one opening of the liquid line is one of a plurality of openings of the liquid line, Wherein only one opening is arranged in or directly adjacent to one respective channel.

\* \* \* \* \*